United States Patent
Vilkomerson et al.

(10) Patent No.: US 7,963,920 B2
(45) Date of Patent: Jun. 21, 2011

(54) VESSEL FLOW MONITORING SYSTEM AND METHOD

(75) Inventors: David Vilkomerson, Princeton, NJ (US); Thomas A. Chilipka, E. Windsor, NJ (US)

(73) Assignee: DVX, LLC, Princeton, NJ (US)

( * ) Notice: Subject to any disclaimer, the term of this patent is extended or adjusted under 35 U.S.C. 154(b) by 1154 days.

(21) Appl. No.: 10/953,276

(22) Filed: Sep. 29, 2004

(65) Prior Publication Data
US 2005/0070799 A1   Mar. 31, 2005

Related U.S. Application Data

(60) Provisional application No. 60/507,070, filed on Sep. 29, 2003.

(51) Int. Cl.
*A61B 8/00* (2006.01)
(52) U.S. Cl. ......... 600/462; 600/437; 600/454; 600/459
(58) Field of Classification Search .......... 600/454–457, 600/437, 459, 462, 467–468
See application file for complete search history.

(56) References Cited

U.S. PATENT DOCUMENTS

| | | | |
|---|---|---|---|
| 4,227,407 A | 10/1980 | Drost | |
| 5,179,418 A | 1/1993 | Takamiya et al. | |
| 5,289,821 A | 3/1994 | Swartz | |
| 5,488,953 A | 2/1996 | Vikomerson | |
| 5,540,230 A | 7/1996 | Vilkomerson | |
| 5,598,841 A | 2/1997 | Taniji et al. | |
| 5,713,362 A | 2/1998 | Vilkomerson | |
| 5,785,657 A | 7/1998 | Breyer et al. | |
| 5,807,258 A | 9/1998 | Cimochowski et al. | |
| 6,346,081 B1 * | 2/2002 | Vilkomerson | 600/454 |
| 6,437,867 B2 | 8/2002 | Zeylikovich et al. | |
| 6,458,086 B1 | 10/2002 | Franco et al. | |

FOREIGN PATENT DOCUMENTS

WO   WO 99/42039   8/1999
WO   WO 01/89387   11/2001

OTHER PUBLICATIONS

"Slab Definition". Jun. 30, 2010. Dictionary.com.*
International Search Report dated May 27, 2005 for related PCT Application No. PCT/US2004/031838 (5 pages).
David H. Evans & W. Norman McDicken, Signal Detection and Pre-processing: CW and PW Doppler, Doppler Ultrasound—Physics, Instrumentation and Signal Processing, 2000, 97-118,Second Edition, John Wiley & Sons, Ltd., Chichester, England.

* cited by examiner

*Primary Examiner* — Tse Chen
*Assistant Examiner* — Peter Luong
(74) *Attorney, Agent, or Firm* — Plevy & Keene LLP

(57) ABSTRACT

A system for monitoring blood flow confined by at least one vessel wall, the system including: at least one implantable diffraction-grating transducer being embedded within or adjacent to a vessel wall, the diffraction-grating transducer being suitable for emitting ultrasound into or receiving Doppler shifted ultrasound from the blood flow; and, a source for pulse-exciting the implantable diffraction grating; wherein, the Doppler shift is indicative of the blood flow.

22 Claims, 6 Drawing Sheets

VESSEL FLOW MONITORING SYSTEM AND METHOD

RELATED APPLICATION

This application claims priority of U.S. Patent Application Ser. No. 60/507,070, entitled DOPPLER TRANSDUCERS FOR IMPLANTABLE FLOW MONITORING, filed Sep. 29, 2003, the entire disclosure of which is hereby incorporated by reference as if being set forth in its entirety herein.

FEDERALLY SPONSORED RESEARCH OR DEVELOPMENT

This invention was made with government support under Grant HL071359 awarded by NHLBI/NIH. The Government has certain rights in this invention.

FIELD OF INVENTION

The present invention relates generally to methods for measuring scattering fluid, such as blood in artificial and natural vessels in the human body.

BACKGROUND OF INVENTION

Blood flow keeps tissue alive. Accordingly, its measurement and monitoring present a significant medical need. Attempts have been made to develop blood flow measurement in vessels for more than 20 years. Particularly advantageous would be means of measuring flow in vessels inside the body, in either natural blood vessels or artificial blood vessels known in the art as prosthetic grafts.

Grafts, commonly replacing diseased natural blood vessels for example, often fail in a relatively short time. For example, when placed in the leg (60,000 grafts a year) data supports that only about one-third of implants still function after five years, and that one-third of the legs have nonetheless been amputated. More particularly, when first placed, graft flow is often high. With time, however, stenoses in the connecting vessels reduce flow such that blood clots in the graft and the graft "fails". Once a graft fails, the prognosis is grim for a limb sustained by the graft—such that amputation is often necessary.

While methods have been proposed to mount flow-sensors in the body and to notify the outside world of diminished flow by means of such implanted systems, it is believed this long felt need has not yet been met.

Doppler ultrasound is useful for assessing flow. To measure the velocity by Doppler effect, however, the measuring ultrasound beam must have a substantial component of its direction in the direction of flow. More particularly, the Doppler shift frequency, Fdop may be found from:

$$fdop = \left(\frac{v}{\lambda}\right)\cos(\theta), \tag{a}$$

where v is the velocity of the back-scattering material, λ is the wavelength of the ultrasound used, and θ is the angle between the insonifying beam and the velocity vector.

However, when a Doppler transducer is conventionally placed flat against the wall of the vessel, the angle between the insonifying beam from the transducer and the velocity is 90°, such that cos(θ) is zero, yielding no flow information. This has prevented using an embedded Doppler transducer in the wall of a graft: as even if the transducer is only 1 mm in length, when angled at just 30° it cannot fit inside the 0.5 mm wall of a graft.

SUMMARY OF INVENTION

A system for monitoring blood flow confined by at least one vessel wall, the system including: at least one implantable diffraction-grating transducer being embedded within or adjacent to a vessel wall, the diffraction-grating transducer being suitable for emitting ultrasound into or receiving Doppler shifted ultrasound from the blood flow; and, a source for pulse-exciting the implantable diffraction grating; wherein, the Doppler shift is indicative of the blood flow.

BRIEF DESCRIPTION OF THE DRAWINGS

Understanding of the present invention will be facilitated by consideration of the following detailed description of the preferred embodiments of the present invention taken in conjunction with the accompanying drawings, in which like numerals refer to like parts, and.

DETAILED DESCRIPTION OF THE INVENTION

It is to be understood that the figures and descriptions of the present invention have been simplified to illustrate elements that are relevant for a clear understanding of the present invention, while eliminating, for the purpose of clarity, many other elements found in typical ultrasonic transducer systems and methods of making and using the same. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein.

According to an aspect of the present invention, there may be provided transducer arrangements and systems that make flow-monitoring in artificial grafts or vessels practical by utilizing diffraction-grating transducers. These arrangements are characterized by having transducers suitable for being embedded in the walls of an artificial graft or attached in a substantially flat manner to the walls of a vessel.

According to an aspect of the present invention, DGT transducers may be embedded in grafts or placed on the side of vessels so as to allow the use of pulsed excitation for implanted flow sensing to be realized.

According to an aspect of the present invention, configurations including Diffraction Grating Transducers (DGT's), optionally with other transducers, may be used for either pulsed or CW operation, and may be desirable for use for flow monitoring within artificial grafts, or attached to the side of natural vessels.

Where the DGT is parallel to the walls of the graft or vessel (hereafter referred to for simplicity as the graft), such as by being embedded within or placed against such a wall, pulsed excitation rather than a "given frequency" may be used. Moreover, through signal processing, flow through the graft can be determined even when the velocity vector characterizing the flow is not parallel to the vessel wall.

Figure 1:
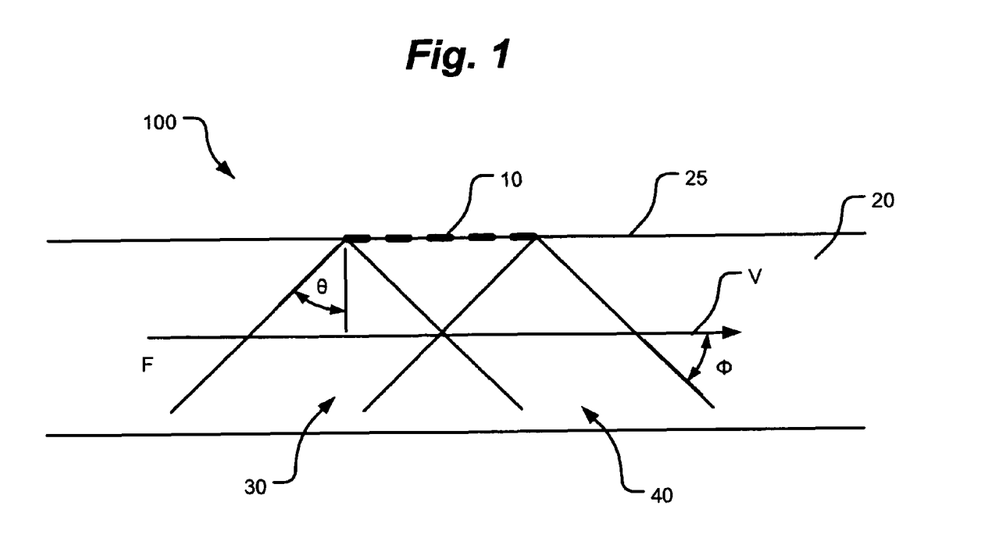
FIGS. 1 and 1A illustrate schematic representations of flow monitoring systems according to an aspect of the present invention.

Referring now to the Figures, wherein like reference characters refer to like elements of the invention, FIG. 1 schematically illustrates an arrangement 100 including a transducer 10 in or attached to the wall 25 of a graft 20. In this and the subsequent drawings, it should be considered that the arrangements are equally representative of a transducer in the wall of an artificial graft or placed flat against the wall of a natural vessel. A diffraction-grating transducer ("DGT"), as discussed in U.S. Pat. Nos. 5,488,953, "Diffracting Doppler-Transducer"; "U.S. Pat. No. 5,540,230, Diffracting Doppler Transducer"; and U.S. Pat. No. 5,713,362, "Higher-Order Quadrature Driven Diffracting Grating Doppler Transducers", the entire disclosures of which are each hereby incorporated by reference herein, (the "DGT patents") is particularly well suited for use in the present invention.

Figure 6:
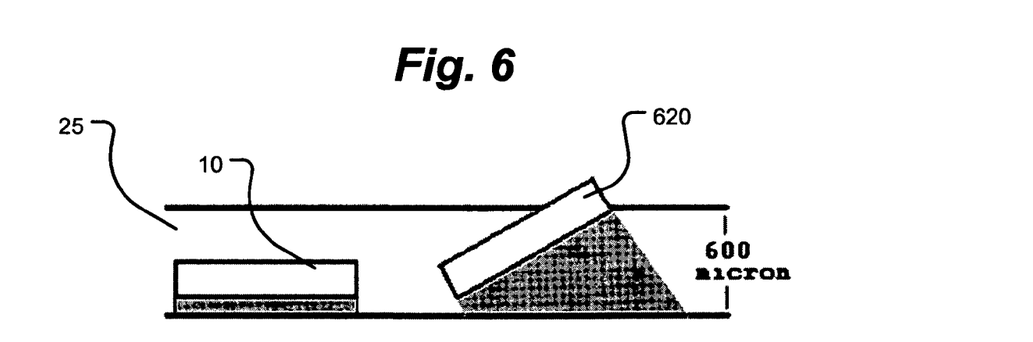
FIG. 6 illustrates a graft wall with a DGT and conventional Doppler transducer associated therewith.

Briefly referring now also to FIG. 6, typical artificial graft walls 25 are 500-600 microns thick. Conventional Doppler transducers 620 must be placed at an angle to the flow; otherwise, the Doppler shift, being proportional to the cosine of the angle between the velocity vector and the beam, would be zero. However, tilting the transducer 620 generally unacceptably broaches the graft wall 25, as is shown in FIG. 6. According to an aspect of the present invention, a DGT transducer 10 may be positioned within a wall 25 of a graft though.

Figure 7:
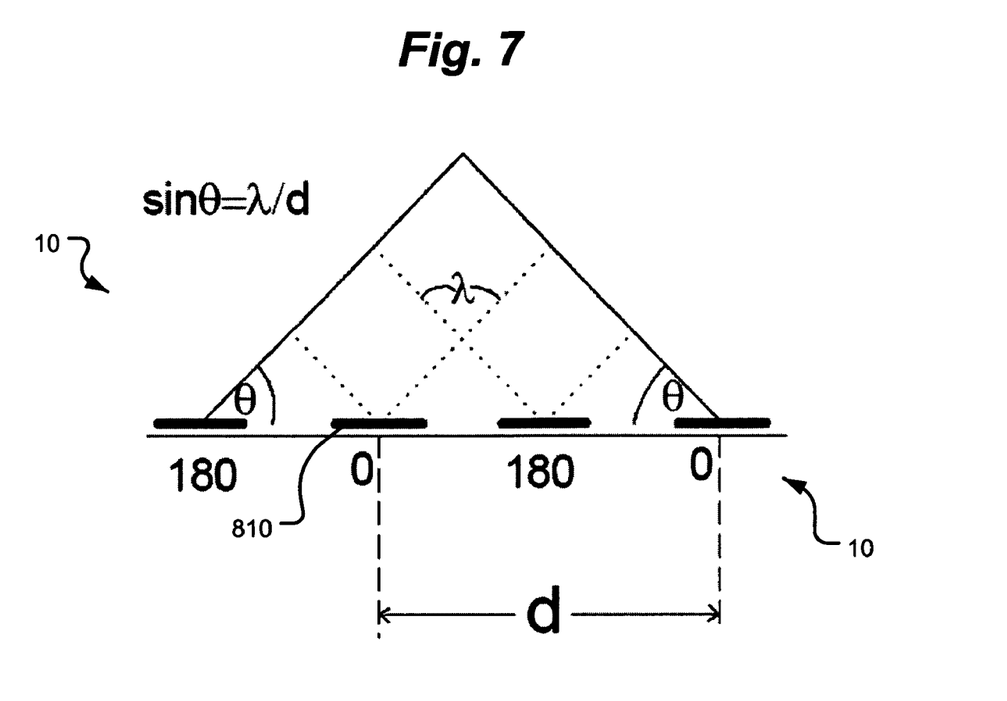
FIG. 7 illustrates a DGT suitable for use according to an aspect of the present invention.

For non-limiting purposes of completeness only, a DGT transducer uses the principle of diffraction to launch beams at an angle to the perpendicular of the transducer's face. This angle (θ), as explained in detail in the DGT patents and illustrated in FIG. 7 hereof, is associated with the wavelength λ of the insonifying beam, and the period d of the spatial arrangement of the individual sub-elements 810 of the transducer. More particularly, $$\theta = \sin^{-1}\left(\frac{n\lambda}{d}\right), \quad (b)$$

where n is usually equal to 1 but, as explained in the afore-incorporated '362 DGT patent, can be equal to an odd number greater than 1 ("Higher order diffraction"). Thus, a DGT transducer can be placed flat inside the walls of a graft or flat on a blood vessel, and still produce a beam non-perpendicular to the flow.

It should be understood however, that while the DGT patents may discuss their use in measuring blood flow, a well-defined driving frequency, typically in the form of either a continuous wave (CW) or long pulse signal (as the bandwidth of a signal is inversely proportional to its duration) has conventionally been used to drive these transducers. This follows from the understanding that unless a single frequency is used, λ is not defined, and therefore, by equation (b), the beam angle θ, required in equation (a) to calculate the velocity, is also not defined.

To fabricate an implantable prosthetic graft, or to develop a small sensor to affix to a blood vessel, simplicity and weight, as well as low power consumption, become critical considerations. As pulsed operation of a Doppler system requires but one transducer and connecting cable, and CW operation requires one transducer and one cable for transmitting and an additional transducer and cable and for receiving, pulsed operation of a DGT used in internal vessels may be desirable in certain applications.

Figure 1A:
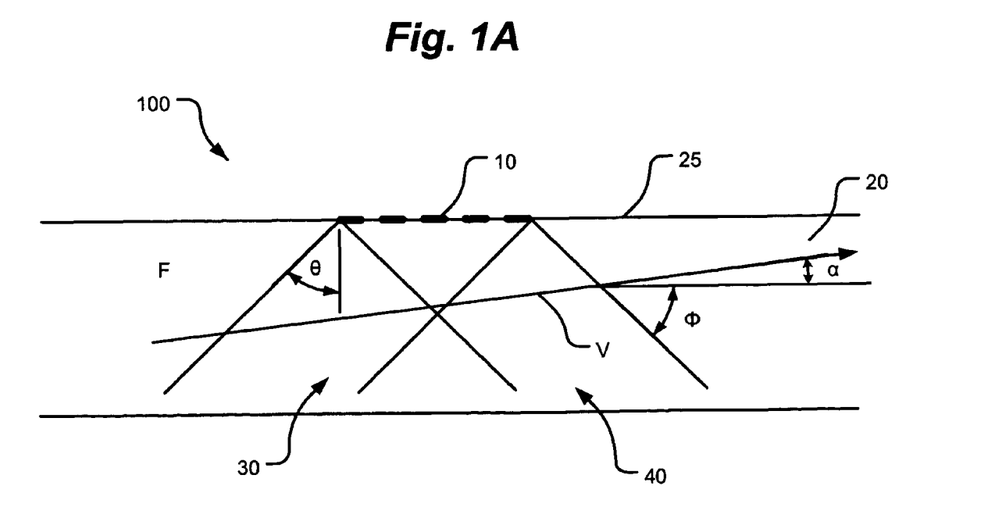

Referring still to FIGS. 1 and 1A, two symmetrical beams 30, 40 may be produced by a 2-element per period DGT 10. FIG. 1 shows these beams 30, 40 impinging on a flow vector V of a fluid F, such as blood, in a vessel. If the velocity vector V is not parallel to the wall of the graft or vessel 20 (as shown in FIG. 1A), the deviation from parallel is shown as α. θ is the insonifying signal angle away from perpendicular, as described in Eq. a. The insonifying signal angle with respect to the velocity vector V is shown as Φ. Arrangement 100 uses a single transducer and connecting cable. Arrangement 100 may be operated in a pulsed mode.

Referring now also to FIGS. 7 and 8, and again for non-limiting purposes of explanation only, DGT 10 may include an array of individual slabs of piezoelectric material, with every other element 810 polarized in the opposite direction. A suitable configuration is shown in FIG. 4 of the afore-incorporated '953 DGT patent. The configuration shown therein may prove desirable in that a single electrode can connect all the elements, simplifying construction. Using a two element per spatial period, rather than a four-element per spatial period allows the elements to be twice as wide as in a 4 element configuration. In such a case, for example, a 60 micron pitch for the elements, as used in the example of a 20 MHz transducer, rather than the 30 micron pitch required for a 4 element per spatial period configuration, may be used. This may serve to make fabrication of such high frequency transducers easier. In other words, a "double-beam" DGT may be used. Such a DGT 10 may include a repeating phase pattern of two elements 810, with relative phase of 0° and 180°. Constructive interference occurs at beam angles of $$\pm\theta = \sin^{-1}\left(\frac{\lambda}{d}\right).$$

Figure 8:
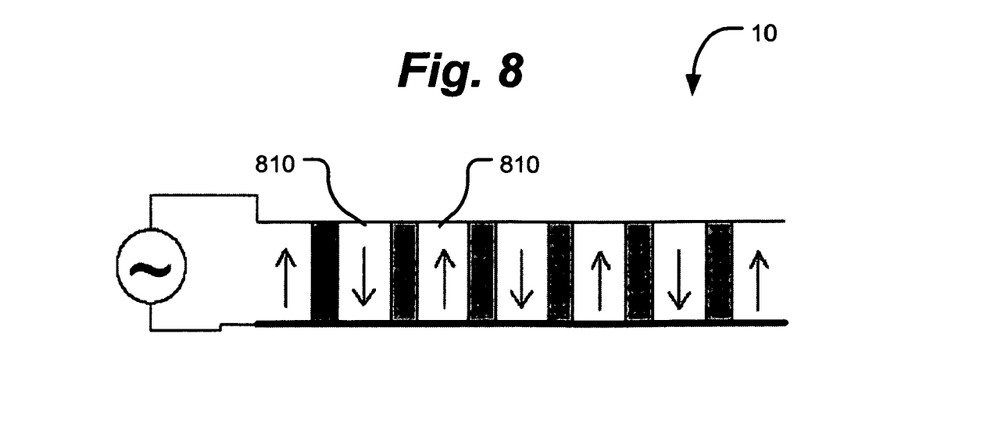
FIG. 8 illustrates an electronic interconnection and DGT according to an aspect of the present invention.

(As the array is symmetrical, two symmetrical beams are formed as would be expected.)

Such a transducer will produce two oppositely-directed beams 30, 40, as shown in FIG. 1, at an angle θ such that:

$$\sin(\theta) = \frac{\lambda}{d}, \quad (1)$$

where λ is the wavelength of the insonifying signal, found from velocity of ultrasound/frequency, and d is the spatial period, i.e., in the case here, the distance between each similarly polarized slab. For example, if driven at a frequency of 20 MHz, the wavelength λ would be 75 microns, and if the spatial period d is 120 microns, sine equals 75/120 or 0.625.

Therefore, two beams will be produced at an angle to the perpendicular, designated θ, of $\sin^{-1}(0.625)$, or ~39°. If the transducer is not parallel to the wall of by an angle γ, the angle θ produced by the element spacing and wavelength λ is adjusted to θ+γ.

Using a double-beam DGT may advantageously permit doubling the ultrasound frequency used: as a double-beam DGT requires only two elements per spatial period, whereas a conventional DGT requires 4 elements per period. If the spacing of the elements (pitch) is the limiting factor in fabricating arrays, the spatial period (d in FIG. 7) for a double-beam DGT is half that of a conventional DGT. By way of further explanation only, in the conventional DGT, the elements are driven in repeating patterns of four, at relative phases of 0°, 90°, 180°, and 270°; all the energy from such a transducer will go into a single beam at the angle of θ from the perpendicular.

Figure 9:
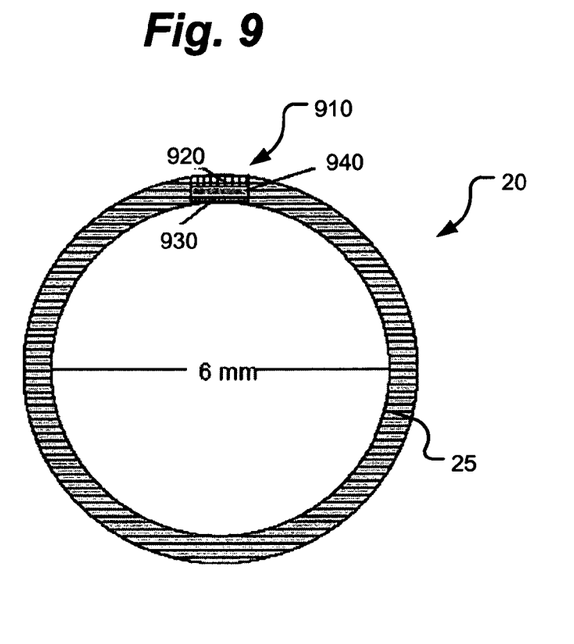
FIG. 9 illustrates a vessel and embedded monitoring transducer system according to an aspect of the present invention; and, FIG. 10 illustrates a system according to an aspect of the present invention.

For the same beam angle, i.e., ratio of λ/d, then, half the wavelength λ can be used. As blood scatters as $\lambda^{-4}$, using half the wavelength produces 16 times as much signal power for the same transmitted power, for a net gain in efficiency of 8 by using the double-beam DGT rather than the conventional DGT. The double-beam DGT has another significant advantage: easier interconnection. By reverse poling every other element 810, as shown in FIG. 8, the required 180° phase shift between elements of FIG. 8 may be simply achieved with sheet electrodes on the top and bottom of the array. A single coax, attached at one end of the transducer, produces the angled beams without any complicated connections to individual elements, an important advantage for a transducer that is to be embedded in the wall 25 of a graft 20, such as is shown in FIG. 9.

Referring again to FIGS. 1 and 1A, the Doppler shift frequency, i.e., the change in frequency caused by moving back scatterers, is given by:

$$fdop = \left(\frac{-2V}{\lambda}\right)\cos\phi, \quad (2)$$

where Φ is the angle between the insonifying ultrasound beam and the velocity vector V.

Short pulses are known to contain a broad array of frequency components, each characterized by a wavelength λ. Where DGT 10 is subjected to short pulse excitation, each such frequency component will appear in a beam at an angle θ—as described by Eq. 1. As DGT 10 is flat with the wall (embedded or placed there) the angle θ and the angle Φ are complements of each other, and their sum is 90°. (Consider the "triangle" at the left of the figure; by symmetry the angle Φ is the complement of θ.) We know from their definitions that the sine of an angle is equal to the cosine of its complement. Therefore, we can write, for Eq. 2:

$$fdop = \left(\frac{-2V}{\lambda}\right)\sin\theta \quad (3)$$

And, substituting for sine from Eq. 1 provides:

$$fdop = \left(\frac{-2V}{\lambda}\right)\left(\frac{\lambda}{d}\right) \quad (3.1)$$

or $$fdop = \frac{-2V}{d}, \quad (4)$$

which is independent of insonifying wavelength λ. Therefore, any frequency used to drive the DGT in this manner, even with the transducer parallel to the wall of the graft or vessel, will produce the same Doppler shift in frequency; such that a short pulse, which contains many frequencies, can be employed with a DGT in this configuration. The resulting Doppler frequency shift, which may be found using conventional methodologies, will characterize the velocity according to Eq. 4. Non-limiting and exemplary methodology for determining the Doppler frequency shift is shown in Doppler Ultrasound, Chapter 6, Evans and McDicken, $2^{nd}$ Ed., 2000, John Wiley & Sons, New York. By way of further example only, one may use a Fourier transform and the recognition that the power in each frequency band corresponds to an amount of blood moving at the velocity that produces that frequency shift.

Thus, one transducer and one cable can be used to measure the flow using arrangement 100 of FIG. 1. As a 20 MHz transducer with 60 micron elements can be very small, for example about 1.5 mm by 1 mm, it may be readily built into a graft and connected to a pacemaker like implant unit to drive and receive the ultrasonic signals. For this configuration, with 60 micron pitch elements constructed with alternate polarizations, as described, the spatial period may be d=120 microns, such that Eq. 4 provides a relation of velocity to Doppler frequency shift as:

$$fdop = \frac{2V}{.120} \text{ (in mm units).} \quad 4.1$$

Or, in more familiar terms, $$fdop = 16.7 \text{ KHz/meter/sec} \quad 4.2$$

Where the flow is not sufficiently parallel to the walls of the vessel, for example in a section of a vessel that occurs after a curved section, as is shown in FIG. 1A, the flow can still be accurately determined. The angle α increases the angle between the beam from the DGT and the velocity vector V on the right to φ+α, and reduces it to φ−α on the left. Using the laws of trigonometry for sums of angles, one may write for the two Doppler-shifted frequencies from the left beam and the right beam as:

$$fdop_{left} = \left(\frac{2V}{\lambda}\right)\{\sin\theta\cos\alpha + \cos\theta\sin\alpha\} \quad 5$$

and from the right beam $$fdop_{rightt} = \left(\frac{2V}{\lambda}\right)\{\sin\theta\cos\alpha - \cos\theta\sin\alpha\} \quad 6$$

By reversing the sign of Eq. 6, summing equations 5 and 6, and dividing by 2, the second terms cancel, resulting in:

$$fdop = \left(\frac{2V}{\lambda}\right)\{\sin\theta\cos\alpha\}. \quad 7$$

Which, by substituting the relation between sin θ and λ of Eq. 1 yields:

$$fdop_{sum} = \left(\frac{2V}{d}\right)\cos\alpha. \qquad 8$$

Consistently, V cos α is exactly the term needed to compute flow, as it is the velocity perpendicular to the cross-section, i.e., when multiplied by the cross-sectional area, it yields the flow rate. Hence, according to an aspect of the present invention, one may accurately measure flow, even where flow is not parallel to the longitudinal axis.

Figure 2:
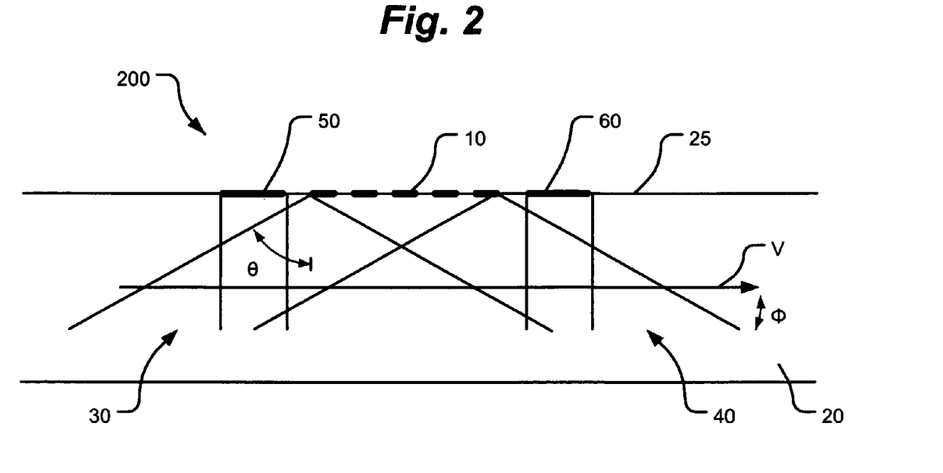
FIGS. 2 and 2A illustrate schematic representations of flow monitoring systems according to another aspect of the present invention.

Referring now also to FIG. 2, there is shown an arrangement 200 utilizing a single DGT 10 and two interconnected "slab" transducers 50, 60. The slab transducers may take the form of small square piezoelectric transducers, by way of non-limiting example only. By way of further non-limiting example only, a simple rectangular, air-backed piece of PZT may be used as a receiver, such as receiver 50, 60. CW ultrasound may be used, such that the "slab" transducer's low bandwidth is unimportant. While this approach may be somewhat more complicated, this arrangement may be operated in either pulsed or CW modes. Further, the arrangement of FIG. 2 does not require a transmit/receive switch in the implant electronics (which must typically be compact for clinical reasons).

Figure 2A:
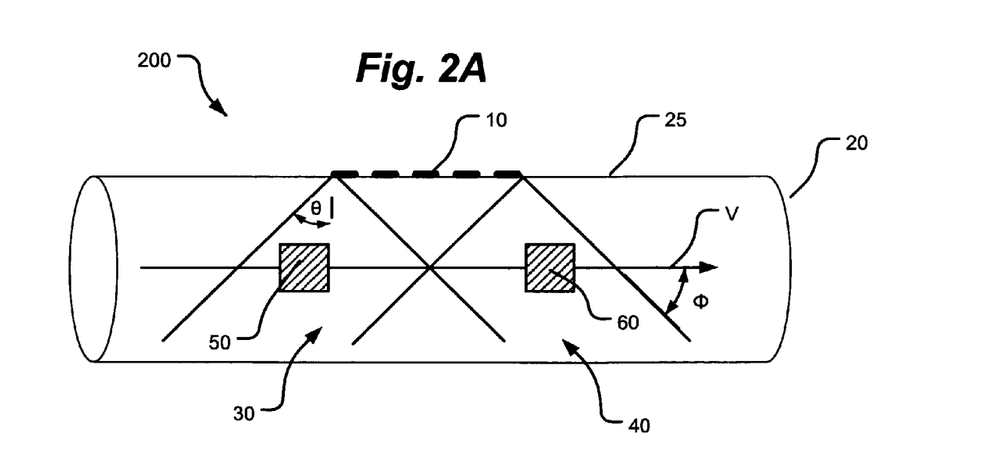

Referring still to FIGS. 2 and 2A, according to an aspect of the present invention, DGT 10 can be used to produce two beams 30, 40, while slab transducers 50, 60 are used to receive the scattered signal. Alternatively, slab transducers 50, 60 can transmit ultrasound signals, while DGT 10 receives ultrasound signals.

As blood scatters ultrasound in all directions, the slab and DGT transducers 50, 60, 10 do not necessarily have to be in the same plane. For example, slab transducers 50, 60 may be rotated 90° around the periphery of graft 20, as is shown in FIG. 2A. Other angles may be utilized as well though. In other words, because blood scatters ultrasound spherically, slab transducers 50, 60 can be in a different plane from that of DGT 10, as shown in FIG. 2A, without a deleterious effect on resulting operation. As will be understood by those possessing an ordinary skill in the pertinent arts, freedom to move the location of the transducers with respect to each other may be useful in fabricating an artificial graft.

While the configuration shown in FIG. 1 may be the simplest in terms of transducers, with one cable and one transducer, it may require more complicated circuitry in terms of a pulsed system, (e.g., pulse shapers, higher voltage drive to attain the same average power, higher bandwidth circuitry, a transmit/receive switch, and a DGT fabricated with a short ring-down period) than a CW operating mode device. When transducers must be driven by implanted circuits, configurations requiring simpler, lower-power circuits may be necessary, even at the expense of more transducers and more cables. Arrangement 200 of FIGS. 2 and 2A can be used for either pulsed or CW modes of operation. In pulsed operation, a transmit/receive switch is not needed; while in CW mode, narrower bandwidths, lower voltage drive, and simpler circuitry may be used. The same geometry of insonifying beams and flow velocity control as has been discussed with regard to FIGS. 1 and 1A, with earlier equations 1-8 being modified so that the factor of two multiplying V (generated by a similar Doppler shift being produced on both transmission and on reception) is replaced by a factor of one—as the scattered ultrasound generated by the moving blood cells are received by the inter-connected slab transducers at right angles to the flow velocity such that no additional Doppler shift is produced on reception.

Figure 3:
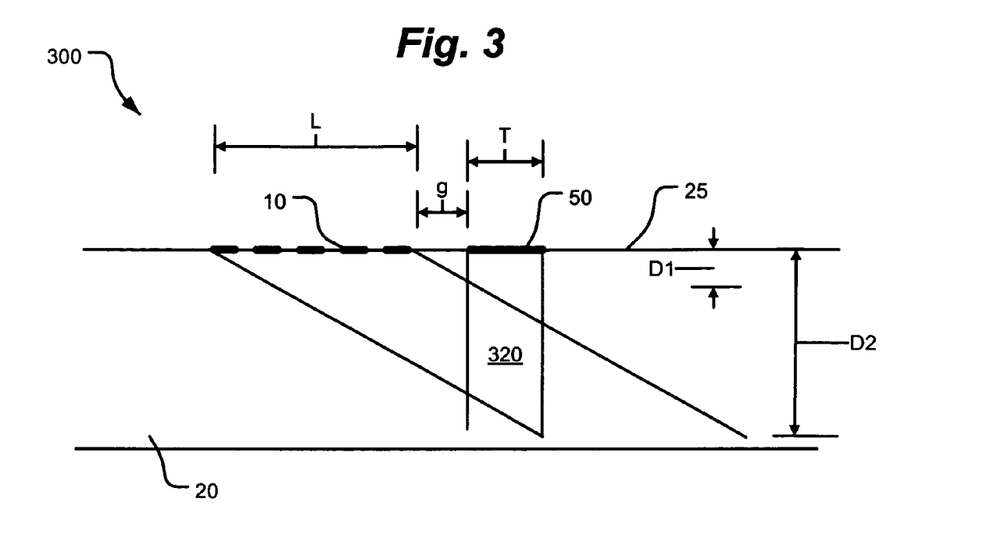
FIG. 3 illustrates a schematic representation of a flow monitoring system according to another aspect of the present invention.

Referring now also to FIG. 3, arrangement 300 illustrated therein is similar to arrangement 200, but with one slab transducer 50 instead of two slab transducers 50, 60. Arrangement 300 may use two cables and operated in either pulsed or CW modes. Again, either transducer may be used as the transmitter and the other as the receiver. Arrangement 300 of FIG. 3 may serve to simplify construction, as compared to arrangement 200.

Arrangement 300 of FIG. 3 can also be used in either CW or pulse modes. It has the additional advantage of using only one slab transducer 50, and potentially occupying less length than arrangement 200. It may suffer the disadvantage of not being able to cancel out the effect of non-parallel flow, as described when two symmetrical beams were available, and produces only half the signal power of the double-slab configuration of arrangement 200.

Advantageously however, because arrangement 300 is not symmetrical in nature, as are arrangements 100, 200, the direction of blood flow can be determined by the Doppler shift frequency. Referring still to FIG. 3, there is also shown how to calculate the sensitive volume, i.e., the region 320 in the graft or vessel in which moving blood will create a Doppler shift signal.

By trigonometry, $$d1 = \frac{g}{\tan\theta} \text{ and } d2 = \frac{(g+T+L)}{\tan\theta} \qquad 9$$

where d1 is the top of the sensitive volume, d2 is the bottom of the sensitive volume, g is the gap between DGT 10 and slab transducer 50, T is the length of the slab transducer 50, and L is the length of DGT 10, which is producing a beam at angle θ to the perpendicular. The height of the sensitive volume, sv, is therefore d2−d1, or $$sv = \frac{(T+1)}{\tan\theta}. \qquad 10$$

For example, using the 1.5 mm long ("L") 20 MHz DGT transducer 10 with a beam angle of θ=39° described previously, with a 1.5 mm long ("T") slab transducer 50 placed 0.5 mm ("g") from DGT 10, the equations above show that the sensitive volume will begin at d1=0.6 mm from the graft wall and extend down to d2=4.4 mm. Consistently, the sensitive volume will include the center of the graft where the velocity needed to calculate the flow is found. While shown for the single slab, these same equations hold for the two sensitive volumes created in arrangement 200 as well.

Figure 4:
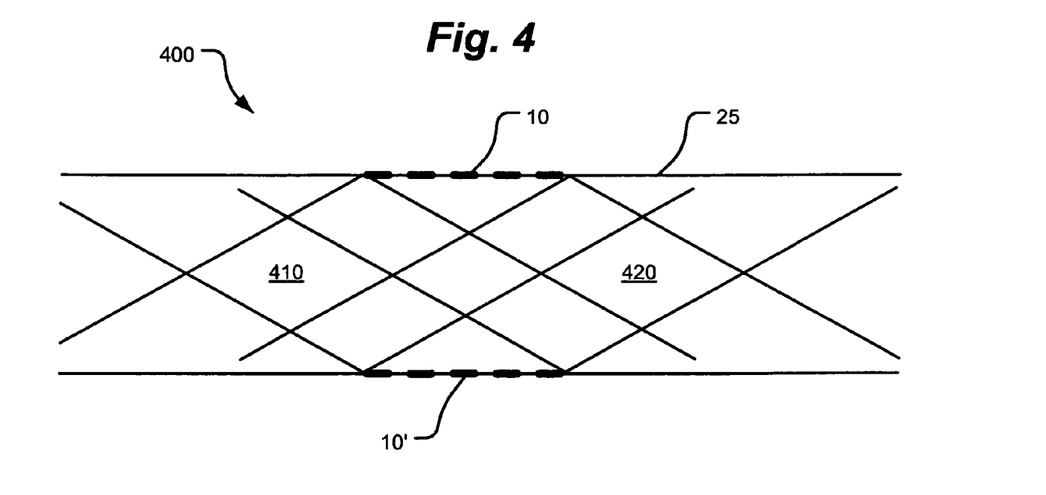
FIG. 4 illustrates a schematic representation of a flow monitoring system according to another aspect of the present invention.

Referring now also to FIG. 4, there is shown an arrangement 400 according to an aspect of the present invention. Arrangement 400 of FIG. 4 uses two DGT's 10, 10' and two cables. Arrangement 400 of FIG. 4 may be operated in either pulsed or CW modes. Arrangement 400 of FIG. 4 may advantageously be used to determine a direction of flow as well.

While requiring two transducers and two cables, as do arrangements 200, 300, arrangement 400 of FIG. 4 has two DGT's 10, 10' and may provide the advantage of shorter overall length, possibly consistent with that of arrangement 100. Unlike arrangement 100 though, arrangement 400 of FIG. 4 may be used in a CW mode, with one DGT transmitting and one receiving.

Furthermore, by using two cables to drive or receive from one of DGT's 10, 10', the direction of flow can be determined: as discussed in the afore-incorporated '230 patent. For non-limiting purposes of completeness only, by driving one subset (every other element) with a signal whose phase is 90° leading or lagging the signal driving the other subset of elements, a single beam (rather than the double beam) is produced in one direction, left or right depending on whether the phase is leading or lagging. By then noting the direction of the Doppler shift, the direction of the flow can be determined, e.g., if the flow is going left to right, and the generated beam is going to the left, the Doppler shift will be higher, while if the flow is right to left, it will be lower. By changing the phase relation between the driving signals, i.e., sending a beam to the right and then to the left, both: (1) the direction (from the change in Doppler shift), as well as (2) the velocity parallel to the wall, independent of the angle of the flow, can be obtained using the same method of calculation with the Doppler result of the two beams as described in relation to arrangement 100. Regions 410, 420 illustrate sensitive volumes for measurement.

Figure 5:
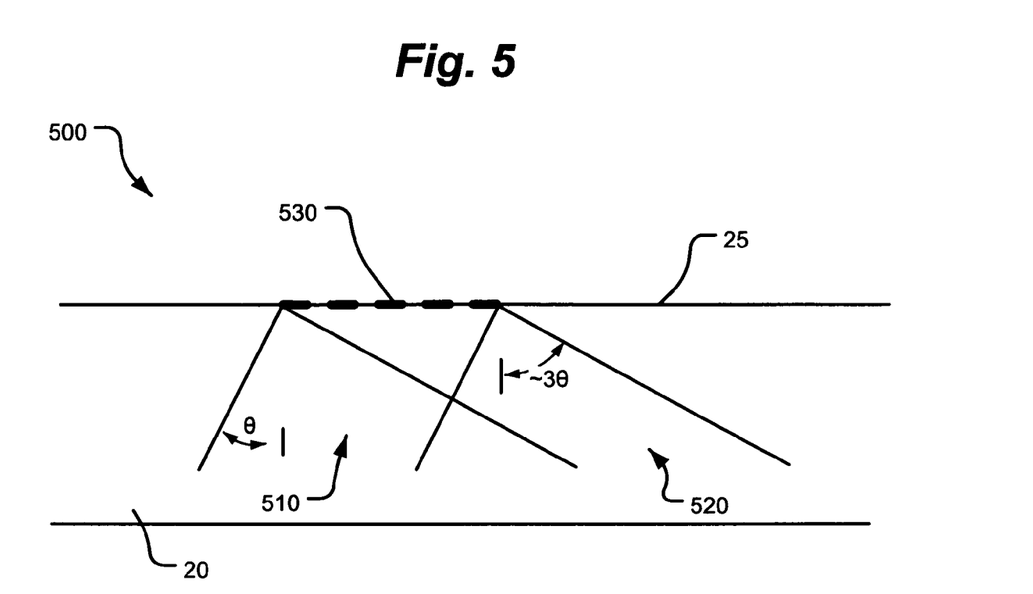
FIG. 5 illustrates a schematic representation of a flow monitoring system according to another aspect of the present invention.

Referring now also to FIG. 5, there are shown beams 510, 520 emanating from a higher-order diffraction grating transducer (H-O DGT) 530 as described in the afore-incorporated '362 DGT patent. While utilizing two cables and operating in a pulsed mode, the illustrated arrangement 500 allows one to ascertain the direction as well as velocity of the flow, and may prove particularly useful in connection with heavily curved vessels, by way of non-limiting example only. In general, H-O DGT 530 can be used in place of DGT 10 described in each of the described arrangements 100-400, inclusive.

Referring still to FIG. 5, there are shown the beams 510, 520 produced by higher-order DGT ("H-O DGT") 530. By driving two sub-grids of a DGT designed according to the '362 patent at a 90° phase shift, two beams 510, 520, one at approximately three times the angle of the other beam's angle, will be produced. Depending upon which grid is driven in phase-advance of the other, either the left-going or the right-going beam will be at an angle whose sine is three times that of the beam of the usual angle, i.e., one beam will be at the angle $$\sin^{-1}\left(\frac{3\lambda}{d}\right),$$

known as the higher-order beam, while the other is at the usual $$\sin^{-1}\left(\frac{\lambda}{d}\right).$$

Arrangement 500 of FIG. 5 may use two cables to drive the individual sub-grids. However, where beams 510, 520 are not symmetric, the direction of flow can be calculated by "flipping" the beams, i.e., changing which cable is 90° ahead in phase, and seeing how the Doppler frequency shift changes. Again, the beam that is going in the direction of flow and is at a higher angle will have the greater Doppler shift.

Therefore, a H-O DGT can be used in place of a DGT in all of arrangements 100-400, with the potential drawback that two cables are used rather than a single cable for a DGT. However, the direction of flow may be calculated using the asymmetry in beam directions.

Another advantage of the H-O DGT in these configurations may lie in using such a transducer where the flow vector changes directions on the two sides of the transducer, e.g., on a curve in a vessel, because the angle of the velocity can be determined independently on each side of the H-O DGT.

By way of further non-limiting explanation only, two Doppler equations with two unknowns of V and $\alpha$ can be determined for each side (left and right) independently. For example, on the left using:

$$fdopl1 = \left(\frac{V1}{\lambda}\right)\cos\left\{90° - \sin^{-1}\left(\frac{\lambda}{d}\right) + \alpha\right\}. \qquad 11$$

After changing the phase relation between the two drives, which can be done in microseconds while the flow remains constant, $$fdopl2 = \left(\frac{V1}{\lambda}\right)\cos\left\{90° - \sin^{-1}\left(\frac{3\lambda}{d}\right) + \alpha\right\}, \qquad 12$$

which two equations when solved simultaneously will yield both V1 and $\alpha$.

Meanwhile, on the right, the same phase-shifting sequence would produce:

$$fdopr1 = \left(\frac{-V2}{\lambda}\right)\cos\left\{90° - \sin^{-1}\left(\frac{3\lambda}{d}\right) + \beta\right\} \qquad 13$$

and $$fdopr2 = \left(\frac{-V2}{\lambda}\right)\cos\left\{90° - \sin^{-1}\left(\frac{\lambda}{d}\right) + \beta\right\}, \qquad 14$$

yielding V2 and $\beta$, which when solved simultaneously provide V1, V2, $\alpha$ and $\beta$, which characterize the independent flow vectors on the right and left of the H-O DGT. Finally, the separate signals from left and right can be separated by virtue of their difference in sign, i.e., the left beams produce the opposite shift in frequency than the right beams, so the two signals for left and right can be discriminated.

Thus, herein are disclosed various configurations of DGT's, H-O DGT's, and optionally conventional non-diffracting transducers, that have particular utility for implanted measuring and monitoring of flow, either by placement onto natural vessels or by being embedded in artificial grafts.

Referring again to FIG. 9, and by way of further non-limiting example only, a 20 MHz double-beam DGT may be used. The elements may be about: 40 microns wide on 60 microns centers, and 70 microns thick. The DGT may be about 1 mm high by 1.5 mm long, and produce two beams at 39° to the perpendicular (in accordance with equation 1), with a round-trip insertion loss of ~18 dB. A slab transducer of $\lambda/4$ PZT 5-H measuring 1 mm high and 1.5 mm long may be mounted next to the DGT on a 200 micron thick base of Macor brand ceramic. Two 160-micron coaxes may be connected, one for drive and one for receive. The completed transducer assembly 910, which may be about the size of a grain of rice, may be embedded in a graft 20 wall 25. Calculated flow rate may be over a range of flows from about 100 to 900 ml/min (which covers the expected range of blood flow in the graft). Less than 500 microwatts may be necessary to drive such a device.

Figure 10:
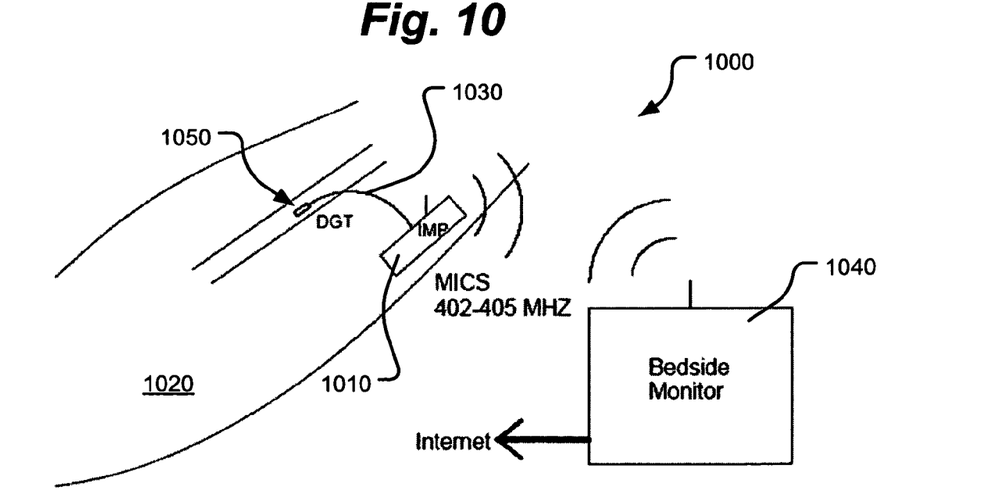

Referring now also to FIG. 10, by way of further, non-limiting example only, a flow monitoring system 1000 may be configured as follows. An implant 1010 may include a transceiver and associated antenna having the following characteristics.

| Parameter | Specification |
| --- | --- |
| Technology | 0.18 um RF CMOS |
| Supply Voltage | 2.1-3.6 volts |
| Radio Frequency | 402-405 MHz (10 ch.) |
| Max Data Rate | 800 kbps |
| Max Sensitivity | −94 dBm |
| Current (TX/RX) | 5 mA |
| Current (Sleep + sniffing) | <200 nA |
| Estimated Range | >2 Meters |
| Bit Error Rate | <10-9 errors/bit |

For example, a suitable transceiver is made by Zarlink, and is similar to the transceiver and antenna presently being used in a commercially available "video capsule" that transmits video images from inside a patient's gastrointestinal system.

Implant 1010 may use a commercially available pacemaker battery of 8 Watt-hour capacity (such as a Wilson Greatbatch LithiumNanadium Silver Oxide Cell 8760) whose size is associated with the implant's size as 25×48×8 mm. Implant 1000 may have an operational life of 10 years on one battery (which can be replaced).

Referring now also to FIG. 9, prior to insertion into a patient, graft wall 25 may be cut back, a transducer embedded and then the remaining cavity backfilled, using a polymer 920. The embedded transducer may include a transducer body itself 930 and support 940. Alternatively, a DGT may be secured to wall 25 using an adhesive strip or loop of a suture, for example.

For artificial graft placement in a leg, implant 1010, which may be similar in size to a pacemaker, may be placed in the thigh 1020, and connected by two thin coaxes 1030 to embedded transducer system 1050 in graft 20. Transducer system 1050 may take the form of any of arrangements 100-500, inclusive.

While the patient is sleeping (so that activity will not affect flow) implanted unit 1010 may drive system 1050 for a few seconds. The received signal may be conventionally processed in implant 1010, i.e., mixed with the drive frequency to obtain baseband I & Q signals, amplified over the band of interest (100 Hz-13 KHz), sampled and digitized at 10 bits at 40 KHz. The resulting data, which may be on the order of 250 Kbytes, may be stored in memory, and then transmitted wirelessly to a bedside monitor 1040. Transmission may occur utilizing the special Medical Implant Communication Service, the 402-405 MHz band the FCC reserves for such use, for example. Bedside monitor 1040 may process the transmitted data to calculate the flow volume, and determine if the calculated flow rate appears valid, e.g., the flows for each cardiac cycle are similar, and that the velocity waveforms are regular. If the data are valid, and the flow within the expected range, bedside monitor 1040 may transmit a signal to implant 1000 to "go to sleep" for 24 hours. If the data are not in the expected range or appear unreliable, implant 1000 may be instructed to operate for another few seconds, to acquire additional Doppler data. If monitor 1040 determines that the flow has been reduced below a threshold, or that the rate of fall of flow is ominous, bedside monitor 1040 may send an e-mail message, or otherwise alert, suitable personnel, such as an attending physician, who may then intervene, for example.

Those of ordinary skill in the art may recognize that many modifications and variations of the present invention may be implemented without departing from the spirit or scope of the invention. Thus, it is intended that the present invention covers the modifications and variations of this invention provided they come within the scope of the appended claims and their equivalents.

What is claimed is:

1. A system for monitoring blood flow confined by at least one wall of a vessel, the system comprising;
    at least one implantable diffraction-grating transducer, said diffraction-grating transducer configured for being implanted on or within and parallel to a wall of a vessel through which blood flows, said diffraction-grating transducer being configured for emitting an ultrasound beam into the blood flow;
    a source configured for exciting said implantable diffraction-grating transducer to cause said ultrasound emission, wherein said excitation source creates a driving signal of one or more frequency components; and
    at least one implantable substantially planar slab transducer configured for being implanted on or within and parallel to the wall of the vessel, said at least one substantially planar slab transducer configured for receiving at substantially right angles relative to the wall of the vessel said ultrasound emissions including Doppler-shifted signals scattered from blood passing through said ultrasound beam produced by said at least one diffraction-grating transducer, the Doppler shift indicative of the scattering blood velocity.

2. The system of claim 1, wherein said received ultrasound signals are indicative of the blood flow to be measured and Doppler shifted with respect to said transmitted ultrasound signals.

3. The system of claim 1, wherein said received ultrasound signals are further indicative of a blood flow direction.

4. The system of claim 1, wherein said at least one substantially planar slab transducer is in a different plane from said at least one diffraction-grating transducer.

5. The system of claim 1, wherein said vessel is an artificial graft.

6. The system of claim 1, wherein said Doppler shift is frequency independent.

7. The system of claim 1, wherein said at least one diffraction-grating transducer comprises a plurality of diffraction-grating transducers.

8. A system for monitoring blood flow confined by at least one wall of a vessel, the system comprising:
    at least one implantable diffraction-grating transducer, said diffraction-grating transducer configured for being disposed adjacent and parallel to a wall of a vessel through which blood flows, said diffraction-grating transducer being configured for emitting an ultrasound beam into the blood flow; and
    a source configured for exciting said implantable diffraction-grating transducer to cause said ultrasound emission, wherein said excitation source creates a driving signal of one or more frequency components; and
    at least one implantable substantially planar slab transducer configured for being implanted adjacent and parallel to the wall of the vessel, said at least one substantially planar slab transducer configured for receiving at substantially right angles relative to the wall of the vessel said ultrasound emissions including Doppler-shifted signals scattered from blood passing through said ultrasound beam produced by said at least one diffraction-grating transducer, the Doppler shift indicative of the scattering blood velocity.

9. The system of claim 8, wherein said received ultrasound signals are indicative of the blood flow to be measured and Doppler shifted with respect to said transmitted ultrasound signals.

10. The system of claim 9, wherein said received ultrasound signals are further indicative of a blood flow direction.

11. The system of claim 8, wherein said at least one substantially planar slab transducer is in a different plane from said at least one diffraction-grating transducer.

12. The system of claim 8, wherein said vessel is an artificial graft.

13. The system of claim 8, wherein said Doppler shift is frequency independent.

14. The system of claim 8, wherein said at least one diffraction-grating transducer comprises a plurality of diffraction-grating transducers.

15. A system for monitoring blood flow confined by at least one wall of a vessel, the system comprising:
- at least one implantable diffraction-grating transducer configured for being implanted on or within and parallel to a wall of a vessel through which blood flows, said diffraction-grating transducer being configured for receiving an ultrasound beam being Doppler shifted by the blood flow;
- at least one substantially planar slab transducer configured for being implanted on or within and parallel to the vessel wall, said at least one substantially planar slab transducer configured for transmitting ultrasound emissions at right angles relative to the wall of the vessel to said at least one diffraction-grating transducer; and
- a source configured for exciting said at least one substantially planar slab transducer to cause said ultrasound emission, wherein said excitation creates an ultrasound emission containing one or more frequency components.

16. The system of claim 15, wherein said received ultrasound signals are indicative of the blood flow to be measured and Doppler shifted with respect to said transmitted ultrasound signals.

17. The system of claim 15, wherein said received ultrasound signals are further indicative of flow direction.

18. The system of claim 15, wherein said vessel is an artificial graft.

19. The system of claim 15, wherein said at least one diffraction-grating transducer comprises a plurality of diffraction-grating transducers.

20. A system for monitoring blood flow confined by at least one wall of a blood vessel, the system comprising:
- at least one implantable diffraction-grating transducer, said diffraction-grating transducer configured for being disposed substantially adjacent and parallel to a wall of a vessel through which blood flows, said diffraction-grating transducer being configured for receiving an ultrasound beam being Doppler shifted by the blood flow; and
- at least one implantable substantially planar slab transducer configured for being implanted on or within and parallel to the wall of the vessel, said at least one substantially planar slab transducer configured for transmitting ultrasound emissions at right angles relative to the wall of the vessel to said at least one diffraction-grating transducer; and
- a source configured for exciting said at least one substantially planar slab transducer to cause said ultrasound emission, wherein said excitation creates a signal containing one or more frequency components.

21. The system of claim 20, wherein said received ultrasound signals are further indicative of flow direction.

22. The system of claim 20, wherein said vessel is an artificial graft.

* * * * *